US009938270B2

(12) United States Patent
Bonnet et al.

(10) Patent No.: US 9,938,270 B2
(45) Date of Patent: Apr. 10, 2018

(54) MONO-PHOSPHATE SALT OF 6-FLUORO-2-[4-(PYRIDIN-2-YL)BUT-3-YN-1-YL]IMIDAZO[1,2A]PYRIDINE (DIPRAGLURANT) AND POLYMORPHS THEREOF AS NEGATIVE ALLOSTERIC MODULATOR OF MGLU5 RECEPTOR

(71) Applicant: Addex Pharma S.A., Geneva (CH)

(72) Inventors: Béatrice Bonnet, Saint-Julien-en-Genevois (FR); Sonia Maria Poli, Geneva (CH)

(73) Assignee: Addex Pharma S.A., Geneva (CH)

( * ) Notice: Subject to any disclaimer, the term of this patent is extended or adjusted under 35 U.S.C. 154(b) by 0 days.

(21) Appl. No.: 15/023,764

(22) PCT Filed: Sep. 25, 2014

(86) PCT No.: PCT/EP2014/070492
§ 371 (c)(1),
(2) Date: Mar. 22, 2016

(87) PCT Pub. No.: WO2015/044270
PCT Pub. Date: Apr. 2, 2015

(65) Prior Publication Data
US 2016/0214979 A1 Jul. 28, 2016

(30) Foreign Application Priority Data
Sep. 25, 2013 (GB) .................................... 1317022.0

(51) Int. Cl.
*C07D 471/04* (2006.01)
*A61K 31/437* (2006.01)

(52) U.S. Cl.
CPC .......... *C07D 471/04* (2013.01); *A61K 31/437* (2013.01)

(58) Field of Classification Search
CPC .......................... C07D 471/04; A61K 31/437
See application file for complete search history.

(56) References Cited

U.S. PATENT DOCUMENTS

| 8,101,637 | B2* | 1/2012 | Bessis | C07D 213/56 514/338 |
| 8,674,106 | B2* | 3/2014 | Bonnet | C07D 213/56 546/121 |
| 8,883,826 | B2* | 11/2014 | Bessis | C07D 213/56 514/338 |
| 2009/0124625 | A1* | 5/2009 | Bessis | C07D 213/56 514/249 |

FOREIGN PATENT DOCUMENTS

| WO | 2005/123703 A2 | 12/2005 |
| WO | 2013/139941 A1 | 9/2013 |
| WO | 2013/186311 A1 | 12/2013 |

OTHER PUBLICATIONS

Bastin et al., Org. Process Res. Dev. 4, 427-35 (2000).*
Berge et al., J. Pharm. Sci. 66, 1-19 (1977).*
UK Intellectual Property Office, Search Report issued in corresponding UK Application No. GB1317022.0 dated Mar. 5, 2014 (5 pages)
International Searching Authority, European Patent Office, Search Report and Written Opinion issued in corresponding PCT Application No. PCT/EP2014/070492 dated Nov. 19, 2014 (11 pages).
Jean-Phillipe Rocher et al, mGluR5 negative allosteric modulators overview: a medicinal chemistry approach towards a series of novel therapeutic agents, Current Topics in Medicinal Chemistry, vol. 11, No. 6, Jan. 1, 2011, p. 680-695.
Handbook of pharmaceutical salts: properties, selection, and use, Ed. Stahl Peter Heinrich: Wermuth Camille G., Jan. 1, 2002, Zurich: Verl. Helvetica Chimica Acta; Weinheim: Wiley-VCH, DE, p. 212-217.

\* cited by examiner

*Primary Examiner* — Theodore R. West
(74) *Attorney, Agent, or Firm* — Wood Herron & Evans LLP

(57) ABSTRACT

The present invention relates to crystalline and amorphous forms of 6-fluoro-2-[4-(pyridin-2-yl)but-3-yn-1-yl]imidazo[1,2-a]pyridine mono-phosphate salt and methods of making these solid forms thereof. The invention compounds are modulators of $mGlu_5$ which are useful for the treatment or prevention of central nervous system disorders as well as other disorders modulated by $mGlu_5$ receptors. The invention is also directed to pharmaceutical compositions and the use of such compounds in the manufacture of medicaments, as well as to the use of such compounds for the prevention and treatment of such diseases in which $mGlu_5$ is involved.

19 Claims, 3 Drawing Sheets

MONO-PHOSPHATE SALT OF 6-FLUORO-2-[4-(PYRIDIN-2-YL)BUT-3-YN-1-YL]IMIDAZO[1,2A]PYRIDINE (DIPRAGLURANT) AND POLYMORPHS THEREOF AS NEGATIVE ALLOSTERIC MODULATOR OF MGLU5 RECEPTOR

SUMMARY OF THE INVENTION

The present invention relates to crystalline and amorphous forms of 6-fluoro-2-[4-(pyridin-2-yl)but-3-yn-1-yl]imidazo[1,2-a]pyridine mono-phosphate salt and methods of making these solid forms thereof. The invention compounds are modulators of mGlu$_5$ receptors which are useful for the treatment or prevention of central nervous system disorders as well as other disorders modulated by mGlu$_5$ receptors. The invention is also directed to pharmaceutical compositions and the use of such compounds in the manufacture of medicaments, as well as to the use of such compounds for the prevention and treatment of such diseases in which mGlu$_5$ receptors are involved.

BACKGROUND TO THE INVENTION

6-Fluoro-2-[4-(pyridin-2-yl)but-3-yn-1-yl]imidazo[1,2-a]pyridine is described in PCT patent application WO05123703 (Example 74) as a negative allosteric modulator of the metabotropic glutamate receptor 5 (mGluR$_5$). The compound has the following structure:

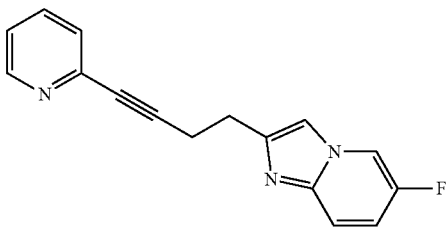 [SMILES: Fc1ccc2nc(CCC#Cc3ccccn3)cn2c1]

The present invention is based on the discovery that the mono-phosphate of 6-fluoro-2-[4-(pyridin-2-yl)but-3-yn-1-yl]imidazo[1,2-a]pyridine exhibits surprisingly much better solubility characteristics as compared to the corresponding free base. The free base has an aqueous solubility of 0.5 mg/mL whereas the mono-phosphate salt has an aqueous solubility of 21.0 to 32.5 mg/mL, at all relevant physiological pH. Thus the increase of the solubility of at least 40 times of the mono-phosphate salt will greatly improve the pharmacological properties of the active compound.

In a first aspect, the present invention relates to the mono-phosphate salt of 6-fluoro-2-[4-(pyridin-2-yl)but-3-yn-1-yl]imidazo[1,2-a]pyridine.

In another aspect, the present invention relates to two distinct crystalline forms, Polymorph I and Polymorph II of the 6-fluoro-2-[4-(pyridin-2-yl)but-3-yn-1-yl]imidazo[1,2-a]pyridine mono-phosphate salt, respectively.

In yet another aspect, the present invention relates to the amorphous form of the 6-fluoro-2-[4-(pyridin-2-yl)but-3-yn-1-yl]imidazo[1,2-a]pyridine mono-phosphate salt.

The aforementioned salt and its crystalline and amorphous forms can be distinguished by physical and chemical properties that can be characterized by X-ray powder diffraction patterns, infrared spectra, melting behavior or glass transition temperatures.

In another aspect, the invention provides a process of preparing the Polymorph I and the Polymorph II of the 6-fluoro-2-[4-(pyridin-2-yl)but-3-yn-1-yl]imidazo[1,2-a]pyridine mono-phosphate salt.

The invention also includes pharmaceutical compositions comprising a therapeutically effective amount of a 6-fluoro-2-[4-(pyridin-2-yl)but-3-yn-1-yl]imidazo[1,2-a]pyridine mono-phosphate salt in a crystalline or in an amorphous form, together with one or more pharmaceutically acceptable carrier, diluent or excipient therefor.

In accordance with the invention the abovementioned crystalline or amorphous forms of the 6-fluoro-2-[4-(pyridin-2-yl)but-3-yn-1-yl]imidazo[1,2-a]pyridine mono-phosphate salt can be used for the preparation of medicaments useful in the control or the prevention of disorders based on the mGlu$_5$ receptor.

DEFINITION OF TERMS

The term "amorphous" as used herein denotes a physical state which is not crystalline and may be verified by X-ray diffraction and other means including but not limited to observation with a polarized light microscope and differential scanning calorimetry (DSC). More particularly, an amorphous salt in accordance with the present invention is preferably essentially free from any crystalline form of 6-fluoro-2-[4-(pyridin-2-yl)but-3-yn-1-yl]imidazo[1,2-a]pyridine mono-phosphate salt.

"Pharmaceutically acceptable" means substantially non-toxic to the subject to which the pharmaceutically acceptable material is administered.

"Therapeutically effective amount" means an amount that is effective to prevent, alleviate or ameliorate the symptoms of disease or prolonge the survival of the subject being treated.

"IR" is used herein as an acronym of InfraRed.

"NMR" is used herein as an acronym of Nuclear Magnetic Resonance.

"XRPD" is used herein as an acronym of X-Ray Powder Diffraction.

DETAILED DESCRIPTION OF THE INVENTION

Figure 1:
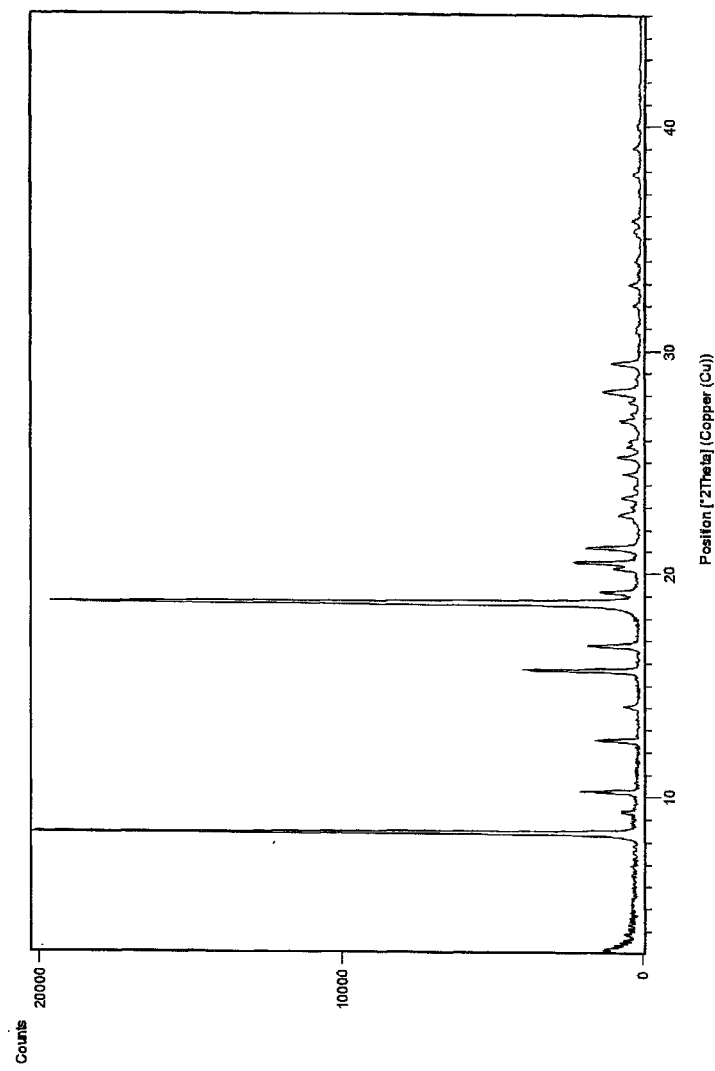
FIG. 1 shows an XRPD pattern of a typical lot of Polymorph I of the mono-phosphate of 6-fluoro-2-[4-(pyridin-2-yl)but-3-yn-1-yl]imidazo[1,2-a]pyridine.

6-Fluoro-2-[4-(pyridin-2-yl)but-3-yn-1-yl]imidazo[1,2-a]pyridine may be prepared as described in PCT patent application WO05123703, which is incorporated by reference herein in its entirety. WO05123703 describes methods of making and using the aforesaid compound.

As already mentioned hereinabove, the present invention relates to novel mono-phosphate salt and to crystalline and amorphous forms of the mono-phosphate salt of 6-fluoro-2-[4-(pyridin-2-yl)but-3-yn-1-yl]imidazo[1,2-a]pyridine.

It has been found that 6-fluoro-2-[4-(pyridin-2-yl)but-3-yn-1-yl]imidazo[1,2-a]pyridine can be isolated, depending upon the method of preparation, as a mono-phosphate salt and that such a salt has an unexpectedly and excellent solubility as a solid and satisfactorily serves as a pharmaceutical.

A further aspect of the present invention is the identification of two different crystal forms of 6-fluoro-2-[4-(pyridin-2-yl)but-3-yn-1-yl]imidazo[1,2-a]pyridine mono-phosphate, identified herein as Polymorphs I and II, respectively.

The mono-phosphate salt of 6-fluoro-2-[4-(pyridin-2-yl)but-3-yn-1-yl]imidazo[1,2-a]pyridine can be prepared by salt formation of 6-fluoro-2-[4-(pyridin-2-yl)but-3-yn-1-yl]imidazo[1,2-a]pyridine with phosphoric acid in methanol with subsequent spontaneous precipitation.

A first polymorph described as "Polymorph I" of 6-fluoro-2-[4-(pyridin-2-yl)but-3-yn-1-yl]imidazo[1,2-a]pyridine mono-phosphate is a solvent-free, crystalline form and may be produced by a process described herein.

Therefore, one aspect of the invention provides a process of preparing Polymorph I of 6-fluoro-2-[4-(pyridin-2-yl)but-3-yn-1-yl]imidazo[1,2-a]pyridine mono-phosphate.

The Polymorph I of 6-fluoro-2-[4-(pyridin-2-yl)but-3-yn-1-yl]imidazo[1,2-a]pyridine mono-phosphate can be obtained by re-crystallization of the mono-phosphate salt in solvent comprising but not limited to ethanol:water (80:20), methanol, isopropyl alcohol:water (80:20), acetonitrile:water (80:20), methanol:dioxane (80:20), methanol:methyl ethyl ketone (80:20 or 60:40), methanol:acetonitrile (60:40), 2-butanone and water:dioxane (10:90).

The Polymorph I of 6-fluoro-2-[4-(pyridin-2-yl)but-3-yn-1-yl]imidazo[1,2-a]pyridine mono-phosphate can be characterized by at least 3 peaks selected from X-Ray diffraction peaks obtained with a $Cu_{K\alpha}$ radiation at 2θ (2 Theta (deg))= 8.4, 10.2, 12.5, 15.7, 16.8, 18.6, 20.5, 21.3, 28.1, 29.4.

The Polymorph I of 6-fluoro-2-[4-(pyridin-2-yl)but-3-yn-1-yl]imidazo[1,2-a]pyridine mono-phosphate can also be characterized by the X-Ray powder diffraction pattern shown on FIG. 1.

The Polymorph I of 6-fluoro-2-[4-(pyridin-2-yl)but-3-yn-1-yl]imidazo[1,2-a]pyridine mono-phosphate can also be characterized by an infrared spectrum having sharp bands at 3059, 2937, 2233, 1592, 1564, 1537, 1515, 1477, 1429, 1317, 1262, 1168, 1162, 1117, 863, 819, 772, 691.

Figure 2:
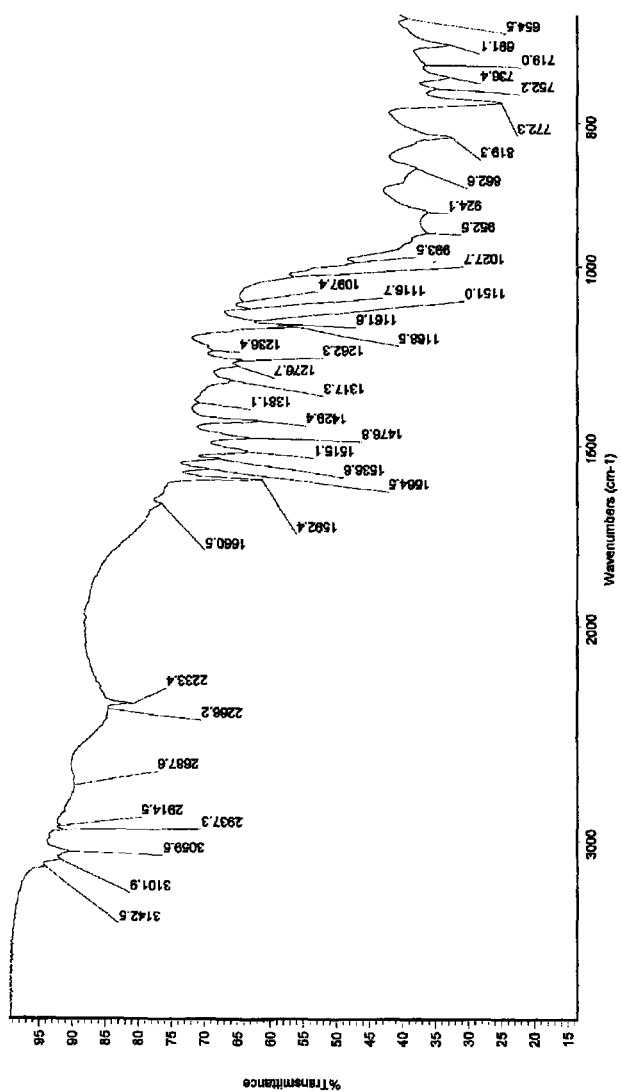
FIG. 2 shows an IR spectrum of a typical lot of Polymorph I of the mono-phosphate of 6-fluoro-2-[4-(pyridin-2-yl)but-3-yn-1-yl]imidazo[1,2-a]pyridine.

The Polymorph I of 6-fluoro-2-[4-(pyridin-2-yl)but-3-yn-1-yl]imidazo[1,2-a]pyridine mono-phosphate can also be characterized by the infrared spectrum shown on FIG. 2.

A second polymorph described as "Polymorph II" of 6-fluoro-2-[4-(pyridin-2-yl)but-3-yn-1-yl]imidazo[1,2-a]pyridine mono-phosphate is a solvent-free, crystalline form and may be produced by a process described herein.

Therefore, one aspect of the invention provides a process of preparing Polymorph II of 6-fluoro-2-[4-(pyridin-2-yl)but-3-yn-1-yl]imidazo[1,2-a]pyridine mono-phosphate.

The Polymorph II of 6-fluoro-2-[4-(pyridin-2-yl)but-3-yn-1-yl]imidazo[1,2-a]pyridine mono-phosphate can be obtained by re-crystallization of the mono-phosphate salt in solvent comprising but not limited to ethanol:water (60:40 or 20:80), methanol:water (20:80), propanol:water (40:60 or 20:80), acetonitrile:water (60:40 or 40:60 or 20:80), acetone:water (20:80) or THF:water (20:80).

The Polymorph II of 6-fluoro-2-[4-(pyridin-2-yl)but-3-yn-1-yl]imidazo[1,2-a]pyridine mono-phosphate can be characterized by at least 3 peaks selected from X-Ray diffraction peaks obtained with a $Cu_{K\alpha}$ radiation at 2θ (2 Theta (deg))=8.5, 10.0, 12.5, 15.8, 17.1, 18.2, 18.7, 19.4, 20.2, 20.8, 25.7, 27.6.

Figure 3:
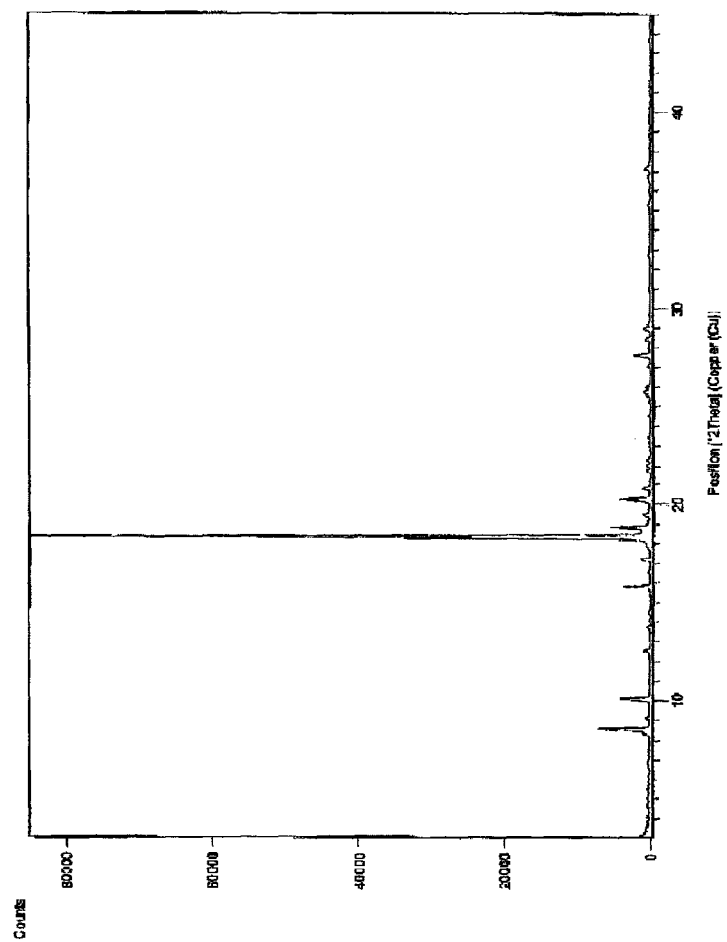
FIG. 3 shows an XRPD pattern of a typical lot of Polymorph II of the mono-phosphate of 6-fluoro-2-[4-(pyridin-2-yl)but-3-yn-1-yl]imidazo[1,2-a]pyridine.

The Polymorph II of 6-fluoro-2-[4-(pyridin-2-yl)but-3-yn-1-yl]imidazo[1,2-a]pyridine mono-phosphate can also be characterized by the X-Ray powder diffraction pattern shown on FIG. 3.

A further aspect of the invention provides a combination of two of the polymorphs described herein.

In accordance with the invention, the crystalline or amorphous forms of the mono-phosphate salt of 6-fluoro-2-[4-(pyridin-2-yl)but-3-yn-1-yl]imidazo[1,2-a]pyridine can be used for the preparation of medicaments useful in the treatment or prevention of disorders in which the $mGlu_5$ receptor plays a role. Such disorders include, but are not limited to: epilepsy, ischemia, neuropathic or inflammatory pain, psychiatric disorders such as psychotic disorders, central nervous system disorders selected from addiction, tolerance or dependence, affective disorders, such as depression and anxiety, attention-deficit/hyperactivity disorder, bipolar disorder, movement disorders, neuroprotection, migraine, neurological disorders such as neurodegeneration, neurotoxicity, Parkinson's disease, PD-LID, dystonia, memory impairment, Alzheimer's disease, dementia, delirium tremens, attentional disorders, eating disorders, mood disorders, cognitive disorders, personality disorders, behavioural disorders, substance of abuse related disorders, including alcohol, nicotine, cocaine, amphetamine, benzodiazepine, analgesics, opiate or other substance tolerance or dependence, bulimia nervosa, anorexia nervosa, gambling dependence, sex dependence, obsessive compulsive disorders, panic disorder, phobia, post-traumatic stress disorder, generalized anxiety disorder, seasonal affective disorders, acute stress disorder, inherited disorders such as Fragile X syndrome, autism, obesity and gastrointestinal disorders, for example, gastro-esophageal reflux disease (GERD), lower esophageal sphincter diseases or disorders, diseases of gastrointestinal motility, colitis, Crohn's disease or irritable bowel syndrome (IBS).

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of dystonia.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of Parkinson's disease L-DOPA induced dyskinesia.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of movement disorders.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of autism.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of Fragile X.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of anxiety.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of depression.

In one preferred embodiment, the polymorphs of the mono-phosphate salt of 6-fluoro-2-[4-(pyridin-2-yl)but-3-yn-1-yl]imidazo[1,2-a]pyridine can be used for the treatment or prevention of pain.

In use for therapy in a mammalian patient, the polymorphs of amorphous forms of the mono-phosphate of 6-fluoro-2-[4-(pyridin-2-yl)but-3-yn-1-yl]imidazo[1,2-a]pyridine defined herein may be administered in the form of a pharmaceutical composition by any route including ingestion, administration by oral, intramuscular, subcutaneous, topical, intranasal, intraperitoneal, intrathoracical, intravenous, epidural, intrathecal, intracerebroventricular routes and by injection into the joints.

In a particular embodiment of the invention, the route of administration may be by ingestion or by an oral, intravenous or intramuscular route.

For preparing pharmaceutical composition from the polymorphs or the amorphous salt of the mono-phosphate of 6-fluoro-2-[4-(pyridin-2-yl)but-3-yn-1-yl]imidazo[1,2-a]pyridine defined herein, inert, pharmaceutically acceptable carriers can be either solid or liquid. Solid form preparations include powders, tablets, dispersible granules, capsules, cachets and suppositories.

A solid carrier can be one or more substance, which may also act as a diluent, a flavoring agent, a solubilizer, a lubricant, a suspending agent, a binder, or a tablet-disintegrating agent; it can also be an encapsulating material.

In powders, the carrier is a finely divided solid, which is a mixture with the finely divided amorphous salt or polymorphs of the mono-phosphate of 6-fluoro-2-[4-(pyridin-2-yl)but-3-yn-1-yl]imidazo[1,2-a]pyridine. In tablets, the active component is mixed with a carrier having the necessary binding properties in suitable proportions and compacted in the shape and size desired.

For preparing suppository compositions, a low-melting wax such as a mixture of fatty acid glycerides and cocoa butter is first melted and the active ingredient is dispersed therein by, for example, stirring. The molten homogeneous mixture is then placed in suitable sized moulds and allowed to cool and solidify.

Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Tablets, powders, cachets, and capsules can be used as solid dosage forms suitable for oral administration by ingestion.

Liquid form compositions include solutions, suspensions, and emulsions. For example, sterile water or water propylene glycol solutions of the active compounds may be liquid preparations suitable for parenteral administration. Liquid compositions can also be formulated in solution in aqueous polyethylene glycol solution.

Aqueous solutions for oral administration can be prepared by dissolving the active component in water and adding suitable colorants, flavouring agents, stabilizers, and thickening agents as desired. Aqueous suspensions for oral use can be made by dispersing the finely divided component in water together with a viscous material such as natural synthetic gums, resins, methyl cellulose, sodium carboxymethyl cellulose, and other suspending agents known to the person skilled in the art.

Depending on the mode of administration, the pharmaceutical composition will preferably include from 0.05% to 99% (percent by weight), more preferably from 0.10 to 50% w, of the amorphous salt or the polymorphs of the mono-phosphate of 6-fluoro-2-[4-(pyridin-2-yl)but-3-yn-1-yl]imidazo[1,2-a]pyridine, all percentages by weight being based on total composition.

The dosage at which the polymorphs or the amorphous salt of the mono-phosphate of 6-fluoro-2-[4-(pyridin-2-yl)but-3-yn-1-yl]imidazo[1,2-a]pyridine according to the invention are administered can vary within wide limits and will, of course, have to be adjusted to the individual requirements in each particular case.

Within the scope of the invention is the use of the polymorphs or the amorphous form of the mono-phosphate of 6-fluoro-2-[4-(pyridin-2-yl)but-3-yn-1-yl]imidazo[1,2-a]pyridine for the manufacture of a medicament.

Also within the scope of the invention is the use of the polymorphs or the amorphous form of the mono-phosphate salt of 6-fluoro-2-[4-(pyridin-2-yl)but-3-yn-1-yl]imidazo[1,2-a]pyridine for the manufacture of a medicament for the therapy of: epilepsy, ischemia, neuropathic or inflammatory pain, psychiatric disorders such as psychotic disorders, central nervous system disorders selected from addiction, tolerance or dependence, affective disorders, such as depression and anxiety, attention-deficit/hyperactivity disorder, bipolar disorder, movement disorders, neuroprotection, migraine, neurological disorders such as neurodegeneration, neurotoxicity, Parkinson's disease, PD-LID, dystonia, memory impairment, Alzheimer's disease, dementia, delirium tremens, attentional disorders, eating disorders, mood disorders, cognitive disorders, personality disorders, behavioural disorders, substance of abuse related disorders, including alcohol, nicotine, cocaine, amphetamine, benzodiazepine, analgesics, opiate or other substance tolerance or dependence, bulimia nervosa, anorexia nervosa, gambling dependence, sex dependence, obsessive compulsive disorders, panic disorder, phobia, post-traumatic stress disorder, generalized anxiety disorder, seasonal affective disorders, acute stress disorder, inherited disorders such as Fragile X syndrome, autism, obesity and gastrointestinal disorders, for example, gastro-esophageal reflux disease (GERD), lower esophageal sphincter diseases or disorders, diseases of gastrointestinal motility, colitis, Crohn's disease or irritable bowel syndrome (IBS).

A further aspect of the invention is a method for therapy of a patient suffering from any of the conditions discussed above, whereby an effective amount of a polymorph or the amorphous form defined herein is administered to a patient in need of such therapy.

Additionally, there is provided a pharmaceutical composition comprising at least one of the polymorphs or the amorphous form of the mono-phosphate of 6-fluoro-2-[4-(pyridin-2-yl)but-3-yn-1-yl]imidazo[1,2-a]pyridine in association with a pharmaceutically acceptable carrier.

Particularly, there is provided a pharmaceutical composition comprising at least one of a polymorph defined herein in association with a pharmaceutically acceptable carrier for therapy, more particularly for therapy of the conditions mentioned herein.

Further, there is provided a pharmaceutical composition comprising at least one of the polymorphs or the amorphous form of the mono-phosphate of 6-fluoro-2-[4-(pyridin-2-yl)but-3-yn-1-yl]imidazo[1,2-a]pyridine in association with a pharmaceutically acceptable carrier use in any of the conditions mentioned herein.

EXPERIMENTAL METHODS

X-Ray-Powder Diffraction (XRPD)

The X-ray powder diffractions pattern was collected using a Philips PW3710 diffractometer (wavelength $\alpha_1$: 1.5406 Å, wavelength $\alpha_2$: 1.54439 Å, Cu source, Voltage 45 kV, filament emission 30 mA). Samples were scanned from 5-50° 2θ and a 2.5 s per step time count.

Differential Scanning Calorimetry (DSC)

Differential Scanning Calorimetry was performed using a Pyris Diamond DSC (Perkin Elmer). A sample (approximately 1-3 mg) was weighed into an aluminium sample pan and transferred to the DSC. The instrument was purged with helium at a flow rate of 20 mL/min and data collected between 30° C. and 250° C., using a heating rate of 10° C./minute.

EXAMPLES

The invention will further be described in more detail by the following Examples which describe methods whereby compounds of the present invention may be prepared, purified and analyzed, and which are not to be construed as limiting the invention.

Example 1: Preparation of the mono-phosphate salt form of 6-fluoro-2-[4-(pyridin-2-yl)but-3-yn-1-yl]imidazo[1,2-a]pyridine 51.0 mg of 6-fluoro-2-[4-(pyridin-2-yl)but-3-yn-1-yl]imidazo[1,2-a]pyridine was dissolved in 2.0 mL of methanol (192.2 μmol). 2.5 mL of 0.1 M Phosphoric acid solution (0.25 mmol of $H_3PO_4$) was added to the methanolic solution of 6-fluoro-2-[4-(pyridin-2-yl)but-3-yn-1-yl]imidazo[1,2-a]pyridine under constant stirring. A clear solution was obtained which then turned into a milky liquid due to the precipitation of the mono-phosphate salt form of 6-fluoro-2-[4-(pyridin-2-yl)but-3-yn-1-yl]imidazo[1,2-a]pyridine. The salt was then allowed to settle down and the supernatant liquid was decanted. The precipitate was dried under the flow of nitrogen and then washed with methanol. The dry solid mono-phosphate salt of 6-fluoro-2-[4-(pyridin-2-yl)but-3-yn-1-yl]imidazo[1,2-a]pyridine was then obtained.

MS m/z $ES^+$=266.2; $^1$H-NMR (500 MHz, DMSO-$d_6$) δ: 10.15 (3H, br s), 8.79-8.75 (1H, m), 8.51 (1H, d), 7.86 (1H, s), 7.76 (1H, t), 7.59 (1H, dd), 7.43 (1H, d), 7.36-7.29 (2H, m), 3.02 (2H, t), 2.88 (2H, t); $^{13}$C-NMR (125.76 MHz, DMSO-$d_6$) δ: 18.49, 27.40, 80.79, 89.89, 111.51, 113.18, 113.51, 116.11, 116.31, 116.45, 116.52, 122.86, 126.84, 136.51, 141.65, 142.73, 145.79, 145.80, 149.74, 151.38, 153.22; IR ($cm^{-1}$): 3102, 3060, 2937, 2915, 2688, 2233, 1592, 1565, 1537, 1515, 1477, 1262, 1169, 819, 772, 752.

Example 2: Preparation of Polymorph-I of 6-fluoro-2-[4-(pyridin-2-yl)but-3-yn-1-yl]imidazo[1,2-a]pyridine mono-phosphate The mono-phosphate salt of 6-fluoro-2-[4-(pyridin-2-yl)but-3-yn-1-yl]imidazo[1,2-a]pyridine (9.5 mg, 26 μmol) was dissolved in 200 mL of a mixture of ethanol:water (80:20) with continuous stirring and gentle warming (30-35° C.) and then filtered to obtain a clear solution. This was then left to crystallize at 5-6° C. The crystallized solid was filtered out and then dried under vacuum to yield the title compound (7.0 mg, 74%).

Example 3: Preparation of Polymorph-II of 6-fluoro-2-[4-(pyridin-2-yl)but-3-yn-1-yl]imidazo[1,2-a]pyridine mono-phosphate 6-Fluoro-2-[4-(pyridin-2-yl)but-3-yn-1-yl]imidazo[1,2-a]pyridine mono-phosphate (10.0 g, 27.3 mmol) was dissolved in 200 mL of a mixture water:acetone (80:20) and was left to stir at 40° C. for an hour, until a clear solution was obtained. Then the solution was kept at 4-6° C. to allow crystallization. The crystals precipitated, then the supernatant was decanted and finally the crystals were dried under vacuum for 12 hours to yield the title compound.

The invention claimed is:

1. A crystalline form of a mono-phosphate salt of 6-fluoro-2-[4-(pyridin-2-yl)but-3-yn-1-yl]imidazo[1,2-a]pyridine.

2. A crystalline form (Polymorph I) of the mono-phosphate salt of claim 1 characterized by at least 3 peaks selected from X-Ray diffraction peaks obtained with a $Cu_{K\alpha}$ radiation at 2 θ (2 Theta (deg))=8.4, 10.2, 12.5, 15.7, 16.8, 18.6, 20.5, 21.3, 28.1, 29.4.

3. A crystalline form (Polymorph I) of the mono-phosphate salt of claim 1 characterized by the X-Ray powder diffraction pattern shown on FIG. 1.

4. A crystalline form (Polymorph I) of the mono-phosphate salt of claim 1 characterized by an infrared spectrum having sharp bands at 3059, 2937, 2233, 1592, 1564, 1537, 1515, 1477, 1429, 1317, 1262, 1168, 1162, 1117, 863, 819, 772, 691 $cm^{-1}$.

5. A crystalline form (Polymorph I) of the mono-phosphate salt of claim 1 characterized by an infrared spectrum shown on FIG. 2.

6. A crystalline form (Polymorph II) of the mono-phosphate salt of claim 1 characterized by at least 3 peaks selected from X-Ray diffraction peaks obtained with a $Cu_{K\alpha}$ radiation at 2 θ (2 Theta (deg))=8.5, 10.0, 12.5, 15.8, 17.1, 18.2, 18.7, 19.4, 20.2, 20.8, 25.7, 27.6.

7. A crystalline form (Polymorph II) of the mono-phosphate salt of claim 1 characterized by the X-Ray powder diffraction pattern shown on FIG. 3.

8. A process for the preparation of a compound according to claim 2, comprising the steps of a) salt formation of 6-fluoro-2-[4-(pyridin-2-yl)but-3-yn-1-yl]imidazo[1,2-a]pyridine with phosphoric acid with subsequent spontaneous precipitation, and re-crystallization of the product of step a) in ethanol:water (80:20) and thereby obtaining a compound of claim 2.

9. A process for the preparation of a compound according to claim 6, comprising the steps of a) salt formation of 6-fluoro-2-[4-(pyridin-2-yl)but-3-yn-1-yl]imidazo[1,2-a]pyridine with phosphoric acid with subsequent spontaneous precipitation, and re-crystallization of the product of step a) in water:acetone (80:20) and thereby obtaining a compound of claim 6.

10. A pharmaceutical composition comprising a therapeutically effective amount of a compound according to claim 1, and at least one pharmaceutically acceptable carrier, diluent or excipient.

11. A method for treating a disorder in which the mGlus receptor plays a role, wherein the disorder is selected from the group consisting of: epilepsy, ischemia, neuropathic or inflammatory pain, a psychiatric disorder selected from psychotic disorders, central nervous system disorders selected from addiction, tolerance or dependence, an affective disorder selected from depression and anxiety, attention-deficit/hyperactivity disorder, bipolar disorder, a movement disorder, migraine, a neurological disorder selected from neurodegeneration, neurotoxicity, Parkinson's disease, PD-LID, dystonia, memory impairment, Alzheimer's disease, dementia, delirium tremens, an attentional disorder, an eating disorder, a mood disorder, a cognitive disorder, a personality disorder, behavioural a behavioral disorder, a substance of abuse related disorders, including alcohol, nicotine, cocaine, amphetamine, benzodiazepine, analgesics, opiate or other substance tolerance or dependence, bulimia nervosa, anorexia nervosa, gambling dependence, sex dependence, obsessive compulsive disorder, panic disorder, phobia, post-traumatic stress disorder, generalized anxiety disorder, seasonal affective disorder, acute stress disorder, an inherited disorders selected from Fragile X syndrome and autism, obesity and a gastrointestinal disorder selected from gastro-esophageal reflux disease (GERD), lower esophageal sphincter diseases, a disease of gastrointestinal motility, colitis, Crohn's disease and irritable bowel syndrome (IBS), comprising the step of administering to a mammalian patient in need of such treatment, an effective amount of a compound according to claim 1.

12. A method for treating dystonia, comprising administering to a mammalian patient in need of such treatment, an effective amount of a compound according to claim 1.

13. A method for treating Parkinson's disease L-DOPA dyskinesia, comprising administering to a mammalian patient in need of such treatment, an effective amount of a compound according to claim 1.

14. A method for treating movement disorders, comprising administering to a mammalian patient in need of such treatment, an effective amount of a compound according to claim 1.

15. A method for treating autism, comprising administering to a mammalian patient in need of such treatment, an effective amount of a compound according to claim 1.

16. A method for treating Fragile X, comprising administering to a mammalian patient in need of such treatment, an effective amount of a compound according to claim 1.

17. A method for treating anxiety, comprising administering to a mammalian patient in need of such treatment, an effective amount of a compound according to claim 1.

18. A method for treating depression, comprising administering to a mammalian patient in need of such treatment, an effective amount of a compound according to claim 1.

19. A method for treating pain, comprising administering to a mammalian patient in need of such treatment, an effective amount of a compound according to claim 1.

* * * * *

UNITED STATES PATENT AND TRADEMARK OFFICE
CERTIFICATE OF CORRECTION

PATENT NO. : 9,938,270 B2  
APPLICATION NO. : 15/023764  
DATED : April 10, 2018  
INVENTOR(S) : Béatrice Bonnet et al.

Page 1 of 1

It is certified that error appears in the above-identified patent and that said Letters Patent is hereby corrected as shown below:

In the Specification

Column 3, Line 1, "unexpectedly" should be --unexpected--.

In the Claims

Claim 11, Column 8, Line 59, "mGlus" should be --mGLu$_5$--.

Claim 11, Column 9, Line 5, "behavioural" should be --behavioral--.

Signed and Sealed this  
Sixteenth Day of April, 2019

Andrei Iancu  
*Director of the United States Patent and Trademark Office*